US006906177B1

(12) United States Patent
Kimura et al.

(10) Patent No.: US 6,906,177 B1
(45) Date of Patent: Jun. 14, 2005

(54) GABA TRANSPORTER PROTEIN AND DNA THEREOF

(75) Inventors: Hiroyuki Kimura, Osaka (JP); Junichi Sakamoto, Osaka (JP); Hidekazu Sawada, Osaka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 561 days.

(21) Appl. No.: 10/009,693

(22) PCT Filed: Jun. 8, 2000

(86) PCT No.: PCT/JP00/03720

§ 371 (c)(1),
(2), (4) Date: Dec. 10, 2001

(87) PCT Pub. No.: WO00/77045

PCT Pub. Date: Dec. 21, 2000

(30) Foreign Application Priority Data

Jun. 10, 1999 (JP) ............................................ 11-163924

(51) Int. Cl.[7] ........................ C07K 14/00; A61K 38/00; C12P 21/00
(52) U.S. Cl. ........................ 530/350; 435/69.1; 514/12
(58) Field of Search ....................... 435/69.1; 530/350; 514/12

(56) References Cited

U.S. PATENT DOCUMENTS 5,658,786 A   8/1997  Smith et al. .................. 435/365
5,712,148 A   1/1998  Borden et al. ............ 435/240.2

FOREIGN PATENT DOCUMENTS

WO   WO 9318143 A1 *  9/1993
WO   WO 96/04790        2/1996 .......... A01N/43/04

OTHER PUBLICATIONS

Christiansen et al., "The role of the MoFe protein alpha–125–Phe and beta–125–Phe residues in Azotobacter vinelandii MoFe protein–Fe protein interaction", 2000, Journal of Inorganic Biochemistry, 80, 195–204.*
Sorlie et al., "Mechanistic Features and Structure of the Nitrogenase alpha–Gln–195 MoFe Protein", 2001, Biochemistry, 40, 1540–1549.*
American Peptide Company Inc.,—Product Detail of Crystalline (di–peptide: Trp–Gly).*

Qing–Rong Liu et al. "Molecular Characterization of Four Pharmacologically Distinct a–Aminobutyric Acid Transporters in Mouse Brain"; The Journal of Biological Chemistry (1993) vol. 268, No. 3 p. 2106–2112.
Laurence A. Borden et al. "Molecular Heterogeneity of the y–Aminobutyric Acid (GABA) Transport System" Cloning of Two Novel High Affinity GABA Transporters from Rat Brains. The Journal of Biological Chemistry (1992) vol. 267, No. 29 p. 21098–21104.
Laurence A. Borden, et al. "Cloing and Expression of a Betaine/GABA Transporter from Human Brain" Journal of Neurochemistry (1995) vol. 64, No. 3, p. 977–984.
Tina Bolvig, et al. "Action of Bicyclic Isoxazole GABA analogues on GABA Transporters and Its Relation to Anticonvulsant Activity" Journal of Pharmacology (1999) vol. 375, No. 1–3 P 367–374.
Qing–Rong Liu, et al. "A Family of Genes Encoding Neurotrasnmitter Transporters" Proc.Natl. Acad. Sci. U.S.A. 89, 6639–6643 (1992).
Nelson, et al. FEBS Letters 269 (1), 181–184 (1990).
Guastella, et al Science 249 (4974), 1303–1306 (1990).
Beatriz Lopez–Corcuera et al. "Expression of a Mouse Brain cDNA Encoding Novel y—Amino–butyric Acid Transporter" J. Biol. Chem. 267, 17491–17493. (1992).
Atsushi Yamauchi, et al. "Cloning of Na+–and Cl–dependent Betaine Transporter That Is Regulated by Hypertonicity" J. Biol. Chem. 267, 649–652. (1992).
Rasola, Andrea, et al. "Molecular Cloning and Functional Characterization of a GABA.betaine Transporter from Human Kidney" FEBS Letters 373 (1995) 229–233.

* cited by examiner

Primary Examiner—Robert A. Wax
Assistant Examiner—Suzanne M. Mayer
(74) Attorney, Agent, or Firm—David G. Conlin; John B. Alexander; Edwards & Angell, LLP

(57) ABSTRACT

The present invention provides a novel protein and its use. The protein or its salt, the partial protein, its amide or ester, or salts, and DNA encoding the same can be employed for obtaining antibodies and antisera, constructing the expression system of the protein of the present invention, for constructing the assay system for the GABA transporter activity and screen medicament candidate compounds using the expression system, for making drug design based on the steric structure of GABA transporters, as agents for producing probes or PCR primers in gene diagnosis, for preparing transgenic animals or as pharmaceuticals for the prevention/treatment of genetic disorders.

6 Claims, 2 Drawing Sheets

GABA TRANSPORTER PROTEIN AND DNA THEREOF

FIELD OF THE INVENTION

The present invention relates to a novel protein containing an amino acid sequence, which is the same or substantially the same as the amino acid sequence represented by SEQ ID NO:1 (preferably a protein having a GABA transporter activity; hereinafter sometimes referred to as the protein of the present invention) or its salts, or a DNA encoding the same.

BACKGROUND ART

γ-Aminobutyric acid (GABA), which is an inhibitory neurotransmitter, is released from GABAergic neurons and then removed from extracellular fluids by the action of GABA transporters located in neuronal terminals and glia cells. The mechanism of this active uptake of GABA transporters is most important for determining when neurotransmission has been accomplished.

It is known that a GABA transporter has four subtypes (GAT-1, GAT-2, GAT-3 and BGT-1). GAT-1 and GAT-3 are located in brain and retina, GAT-2 in almost all organs, and BGT-1 in kidney and brain. The GAT-1 gene was cloned from mouse (Gene Bank accession No. M92378), rat (Gene Bank accession No. M33003) and human. (Gene Bank accession No. X54673); the GAT-2 gene from 30 mouse (Gene Bank accession No. L04663) and rat (Gene Bank accession No. M95762); the GAT-3 gene from mouse (Gene Bank accession No. L04662) and rat (Gene Bank accession No. M95763); and the BGT-1 gene from mouse (Gene Bank accession No. M97632) and dog (Gene Bank accession No. M80403). However, a human GAT-2 gene is yet unknown so far.

It is an object of the present invention to provide the following:

(i) a protein containing an amino acid sequence, which is the same or substantially the same as the amino acid sequence represented by SEQ ID NO:1 (preferably, a protein having a GABA transporter activity) or its partial peptide, or its amide or ester, or a salt thereof;

(ii) a DNA encoding the protein containing an amino acid sequence, which is the same or substantially the same as the amino acid sequence represented by SEQ ID NO:1 (preferably, a protein having a GABA transporter activity) or its partial peptide;

(iii) a recombinant vector containing the DNA;

(iv) a transformant bearing the recombinant vector;

(v) a process of producing the protein containing an amino acid sequence, which is the same or substantially the same as the amino acid sequence represented by SEQ ID NO:1 (preferably, a protein having a GABA transporter activity) or a salt thereof;

(vi) an antibody to the protein containing an amino acid sequence, which is the same or substantially the same as the amino acid sequence represented by SEQ ID NO:1 (preferably, a protein having a GABA transporter activity) or its partial peptide, or its amide or ester, or a salt thereof;

(vii) a method of screening a compound that alters a GABA transporter activity of the protein containing an amino acid sequence, which is the same or substantially the same as the amino acid sequence represented by SEQ ID NO:1 (preferably, a protein having a GABA transporter activity), or its salt;

(viii) a compound or its salt obtainable by the screening method; and, (ix) a pharmaceutical comprising the compound or its salt.

DISCLOSURE OF THE INVENTION

The present inventors have made extensive studies and as a result, succeeded in isolating cDNA encoding human-derived GABA transporter protein having a high homology to mouse- or rat-derived GAT-2, sequencing the entire base sequence and then expressing cDNA in cells. Based on these findings, the present inventors have come to accomplish the present invention.

That is, the present invention provides the following:

(1) A protein containing an amino acid sequence, which is the same or substantially the same amino acid sequence represented by SEQ ID NO:1, or its salt.

(2) The protein or its salt according to (1), which has a GABA transporter activity.

(3) A partial peptide of the protein according to (1), its amide or ester, or a salt thereof.

(4) A DNA containing a DNA having a base sequence encoding the protein according to (1) or the partial peptide according to (3).

(5) The DNA according to (4) having a base sequence represented by SEQ ID NO:2.

(6) A recombinant vector containing the DNA according to (4).

(7) A transformant transformed with the recombinant vector according to (6).

(8) A method of producing the protein or its salt, according to (1) or the partial peptide, its amide or ester, or a salt thereof, according to (3), which comprises culturing said transformant according to (7), producing and accumulating the protein according to (1) or the partial peptide according to (3), and collecting the protein or partial peptide.

(9) An antibody to the protein or its salt according to (1) or to the partial peptide, its amide or ester, or a salt thereof according to (3).

(10) A method of screening a compound that promotes or inhibits a GABA transporter activity, which comprises assaying the GABA transporter activity using the protein or its salt according to (1), or the partial peptide, its amide or ester, or a salt thereof according to (3).

(11) A method for screening a compound or its salt that promotes or inhibits a GABA transporter activity of the protein or its salt according to (1), or the partial peptide, its amide or ester, or a salt thereof, according to (3), which comprises using the protein or its salt according to (1), or the partial peptide, its amide or ester, or a salt thereof, according to (3).

(12) A kit for screening a compound or its salt that promotes or inhibits a GABA transporter activity, comprising the protein or its salt according to (1), or the partial peptide, its amide or ester, or a salt thereof, according to (3).

(13) A kit for screening a compound or its salt that promotes or inhibits a GABA transporter activity of the protein or its salt according to (1), or the partial peptide, its amide or ester, or a salt thereof, according to (3), comprising the protein or its salt according to (1), or the partial peptide, its amide or ester, or a salt thereof, according to (3).

(14) A compound or its salt that promotes or inhibits a GABA transporter activity, obtainable using the screening method according to (10) or using the screening kit according to (12).

(15) A compound or its salt that promotes or inhibits a GABA transporter activity of the protein or its salt according to (1), or the partial peptide, its amide or ester, or a salt thereof, according to (3), which is obtainable using the screening method according to (11) or using the screening kit according to (13).

(16) A pharmaceutical product comprising a compound or its salt that promotes or inhibits a GABA transporter activity, which is obtainable using the screening method according to (10) or using the screening kit according to (12).

(17) A pharmaceutical product comprising a compound or its salt that promotes or inhibits a GABA transporter activity of the protein or its salt according to (1), or the partial peptide, its amide or ester, or a salt thereof, according to (3), which is obtainable using the screening method according to (11) or using the screening kit according to (13).

(18) A pharmaceutical product comprising a compound or its salt that promotes or inhibits a GABA transporter activity of the protein or its salt according to (1), or the partial peptide, its amide or ester, or a salt thereof, according to (3), which is a medicament for the prevention/treatment of anxiety, spasm, epilepsy, schizophrenia, cerebrovascular disorders, cerebral palsy, spastic spinal paralysis, spondylosis deformans, spinocerebellar degeneration, spastic paralysis accompanied by multiple sclerosis, tension headache, lumbago, and neck, shoulder and arm syndrome.

(19) A pharmaceutical product comprising a compound or its salt that promotes or inhibits a GABA transporter activity of the protein or its salt according to (1), or the partial peptide, its amide or ester, or a salt thereof, according to (3), which is a medicament for the prevention/treatment of dementia.

More specifically, the present invention provides the following:

(20) The protein or its salt according to (1), wherein the protein is a protein or its salt containing (i) the amino acid sequence represented by SEQ ID NO:1, an amino acid sequence represented by SEQ ID NO:1, wherein at least 1 or 2 (preferably approximately 1 to 30, more preferably approximately 1 to 9 and most preferably several (1 or 2)) amino acids are deleted; (ii) an amino acid sequence represented by SEQ ID NO:1, to which at least 1 or 2 (preferably approximately 1 to 30, more preferably approximately 1 to 10 and most preferably several (1 or 2)) amino acids are added; (iii) an amino acid sequence represented by SEQ ID NO:1, in which at least 1 or 2 (preferably approximately 1 to 30, more preferably approximately 1 to 10 and most preferably several (1 or 2)) amino acids are substituted with other amino acids; and (iv) a combination of the above amino acid sequences.

(21) A method of screening according to (10) or (11), which comprises comparing the case wherein a test compound is contacted with the protein or its salt according to (1), or the partial peptide, its amide or ester, or a salt thereof according to (3), and the case wherein the test compound is not contacted with the protein or its salt according to (1), or the partial peptide, its amide or ester, or a salt thereof according to (3).

(22) A method of screening a compound or its salt that alters a GABA transporter activity, which comprises comparing the case wherein a test compound is contacted with a cell containing the protein according to (1), and the case wherein the test compound is not contacted with the cell containing the protein according to (1).

(23) A method of screening a compound or its salt that alters a GABA transporter activity of the protein according to (1), which comprises comparing the case wherein a test compound is contacted with the protein according to (1) expressed on a cell membrane of the transformant according to (7) by incubation of the transformant, and the case wherein the test compound is not contacted with the protein according to (1) expressed on the cell membrane of the transformant according to (7) by incubation of the transformant.

(24) A compound or its salt that alters a GABA transporter activity of the protein according to (1), which is obtainable by the screening method according to (21) through (23).

(25) A composition for the prevention/treatment of anxiety, spasm, epilepsy, schizophrenia, cerebrovascular disorders, cerebral palsy, spastic spinal paralysis, spondylosis deformans, spinocerebellar degeneration, spastic paralysis accompanied by multiple sclerosis, tension headache, lumbago, and neck, shoulder and arm syndrome, comprising a compound or its salt that alters the function of the protein according to (1), which is obtainable by the screening method according to (21) through (23).

(26) A method for quantification of the protein or its salt according to (1), or the partial peptide, its amide or ester, or a salt thereof according to (3) in a test sample fluid, which comprises contacting the antibody according to (9) with the test sample fluid.

(27) A composition for the prevention/treatment of anxiety, spasm, epilepsy, schizophrenia, cerebrovascular disorders, cerebral palsy, spastic spinal paralysis, spondylosis deformans, spinocerebellar degeneration, spastic paralysis accompanied by multiple sclerosis, tension headache, lumbago, and neck, shoulder and arm syndrome, comprising the antibody according to (9).

BEST MODE FOR CARRYING OUT THE INVENTION

Figure 1:
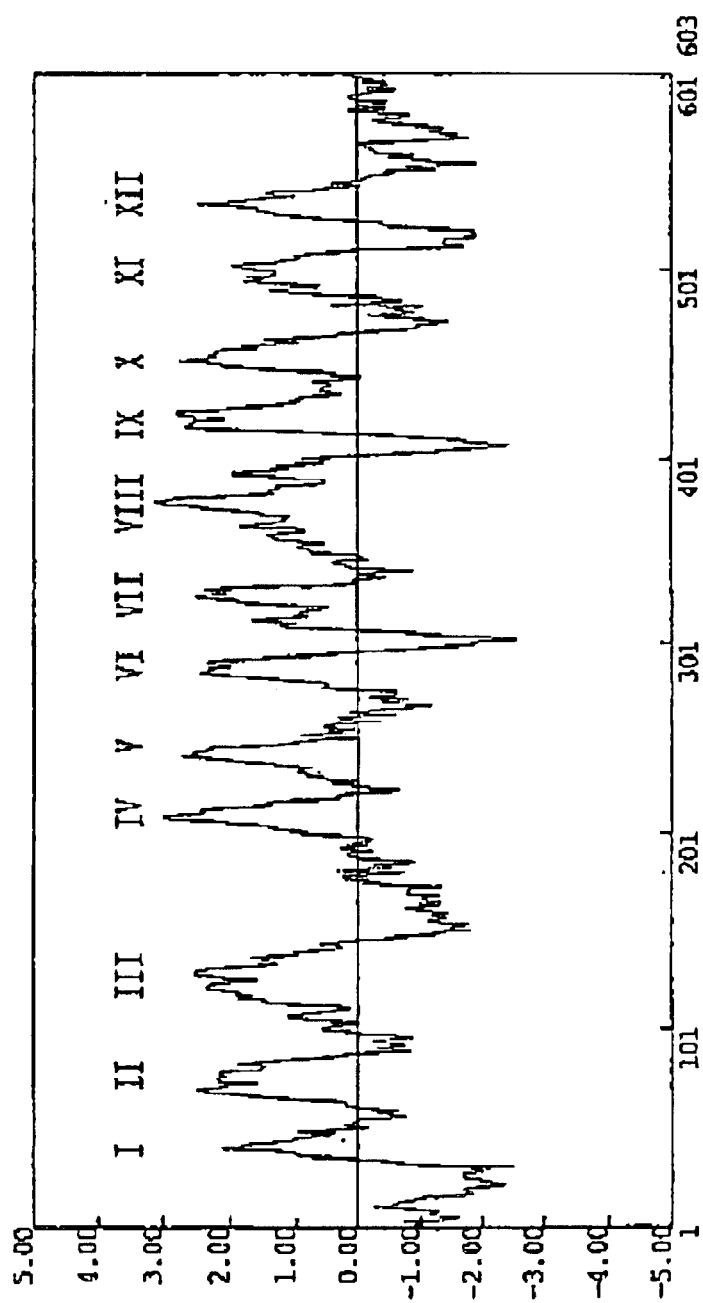
FIG. 1 shows hydrophobic plotting prepared based on the amino acid sequence of the human-derived protein of the present invention, obtained in EXAMPLES.

The protein of the present invention is a protein which has the same or substantially the same as the amino acid sequence shown by SEQ ID NO:1.

The protein of the present invention may be any protein derived from any cells of human and other warm-blooded animals (e.g., guinea pig, rat, mouse, rabbit, swine, sheep, bovine, monkey, etc.) such as splenocyte, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocyte or interstitial cell; or the corresponding precursor cells, stem cells, cancer cells, etc.; or any tissues where such cells are present, such as brain or any of brain regions (e.g., olfactory bulb, amygdaloid nucleus, basal ganglia, hippocampus, thalamus, hypothalamus, subthalamic nucleus, cerebral cortex, medulla oblongata, cerebellum, occipital lobes, frontal lobe, lateral lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, peripheral hemocytes, prostate, testis, ovary, placenta, uterus, bone, joint, skeletal muscle, etc. (especially, brain or any of brain regions); the proteins may also be synthetic proteins.

The amino acid sequence which is substantially the same as the amino acid sequence represented by SEQ ID NO:1 includes, for example, an amino acid sequence having at least about 95% homology, preferably at least about 98% homology, to the amino acid sequence represented by SEQ ID NO:1.

Examples of the protein containing the amino acid sequence which is substantially the same as the amino acid sequence represented by SEQ ID NO:1 include a protein containing the amino acid sequence which is substantially the same as the amino acid sequence represented by SEQ ID NO:1 and has an activity substantially equivalent to that of the amino acid sequence represented by SEQ ID NO:1, etc.

The term "substantially equivalent" is used to mean that the activities of the protein, for example, a transporter activity (GABA transporter activity), physiological properties, etc. are substantially equivalent. Substitution, deletion, addition or insertion of an amino acid(s) do not often cause significant changes in physiological or chemical properties of polypeptides; in such a case, proteins that have undergone such substitution, deletion, addition or insertion will be considered to be substantially equivalent to intact proteins that do not receive undergo the substitution, deletion, addition or insertion. Substantially the same substituent(s) of an amino acid(s) in the amino acid sequence can be selected from, e.g., other amino acids of the class to which the amino acid(s) belong. Examples of non-polar (hydrophobic) amino acids include alanine, leucine, isoleucine, valine, proline, phenylalanine, tryptophan, methionine and the like. Examples of polar (neutral) amino acids are glycine, serine, threonine, cysteine, tyrosine, asparagine, glutamine, and the like. Examples of positively charged (basic) amino acids are arginine, lysine, histidine, and the like. Examples of negatively charged (acidic) amino acids include aspartic acid, glutamic acid, and the like.

The substantially equivalent activities are used to mean that these activities are equivalent in terms of its nature (physiolochemically or pharmacologically). Therefore, it is preferred that these activities are equivalent to each other, but it is allowable that differences among grades such as the level of these activities and molecular weight of the protein may be present.

The transporter activity can be determined according to a publicly known method, for example, by means of screening which will be later described.

As the protein of the present invention, there may be employed proteins containing (i) the amino acid sequence represented by SEQ ID NO:1, of which at least 1 or 2 (preferably approximately 1 to 30, more preferably approximately 1 to 9 and most preferably several (1 or 2)) amino acids are deleted; (ii) the amino acid sequence represented by SEQ ID NO:1, to which at least 1 or 2 (preferably approximately 1 to 30, more preferably approximately 1 to 9 and most preferably several (1 or 2)) amino acids are added; (iii) the amino acid sequence represented by SEQ ID NO:1, in which at least 1 or 2 (preferably approximately 1 to 30, more preferably approximately 1 to 9 and most preferably several (1 or 2)) amino acids are substituted with other amino acids; and (iv) a combination of the above amino acid sequences. Furthermore, examples of the proteins of the present invention include variants of the proteins described above, wherein the amino group at the N-terminal methionine residue of the proteins is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and Gln thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins having sugar chains.

The partial peptides of the proteins of the present invention (hereinafter sometimes merely referred to as the partial peptides) may be any partial peptides so long as they are partial peptides of the proteins of the present invention described above, but exposed extracellularly sites, etc. in the proteins of the present invention may be used.

Specifically, the partial peptides of the proteins containing the amino acid sequence represented by SEQ ID NO:1 are peptides containing the region determined to be an extracellular region (hydrophilic site) in the hydrophilic plotting shown in [FIG. 1]. Peptides containing in part the hydrophobic site may also be employed similarly. Peptides containing respective domains separately may also be employed, and peptides containing the site bearing a plurality of the domains at the same time may be used as well.

Also the partial peptides of the present invention, may be those containing the amino acid sequences described above, of which at least 1 or 2 (preferably approximately 1 to 30, more preferably approximately 1 to 9 and most preferably several (1 or 2)) amino acids are deleted; to which at least 1 or 2 (preferably approximately 1 to 30, more preferably approximately 1 to 9 and most preferably several (1 or 2)) amino acids are added; or, in which at least 1 or 2 (preferably approximately 1 to 30, more preferably approximately 1 to 9 and most preferably several (1 or 2)) amino acids are substituted with other amino acids.

In the partial proteins of the present invention, the C-terminus is usually in the form of a carboxyl group (—COOH) or a carboxylate (—COO⁻) but may be in the form of an amide (—CONH$_2$) or an ester (—COOR) (wherein R has the same significance as defined above).

The partial peptides of the present invention further include those containing substituents on the side chains of intramolecular amino acids, which are protected with appropriate protecting groups, conjugated peptides such as so-called glycoproteins having sugar chains bound thereto, and the like.

The partial peptide of the present invention can be employed as an antigen for producing an antibody and therefore, does not necessarily possess the GABA transporter activity.

As salts of the protein of the present invention or its partial peptide, physiologically acceptable acid addition salts are particularly preferred. Examples of such salts employed are salts with, e.g., inorganic acids (e.g., hydrochloric acid, phosphoric acid, hydrobromic acid, sulfuric acid), or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The protein of the present invention or its salts may be manufactured by a publicly known purification method from human or the other warm-blooded animal cells or tissues described above. Alternatively, the protein of the present invention or its salts may also be manufactured by culturing a transformant containing DNA encoding the protein of the present invention, which will be later described. Furthermore, the protein of the present invention or its salts may also be manufactured by the methods for synthesizing proteins, which will also be described hereinafter, or by a modification of such methods.

Where the protein or its salts are manufactured from human or mammalian tissues or cells, the human or mammalian tissues or cells are homogenized, then extracted with an acid or the like, and the extract is isolated and purified by a combination of chromatography techniques such as reverse phase chromatography, ion exchange chromatography, and the like.

The partial peptide of the protein of the present invention or its salts can be manufactured by publicly known methods for peptide synthesis, or by cleaving the protein of the present invention with an appropriate peptidase. For the methods for peptide synthesis, for example, either solid phase synthesis or liquid phase synthesis may be used. That is, the partial peptide or amino acids that can construct the protein of the present invention are condensed with the remaining part of the partial peptide of the present invention. Where the product contains protecting groups, these protecting groups are removed to give the desired peptide. Publicly known methods for condensation and elimination of the protecting groups are described in 1)–5) below.

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: *Peptide Gosei-no-Kiso to Jikken* (Basics and experiments of peptide synthesis), published by Maruzen Co. (1975)

4) Haruaki Yajima & Shunpei Sakakibara: *Seikagaku Jikken Koza* (Biochemical Experiment) 1, *Tanpakushitsu no Kagaku* (Chemistry of proteins) IV, 205 (1977)

5) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the above methods is in a free form, the peptide can be converted into an appropriate salt by a publicly known method or a modification of the known method; conversely when the protein is obtained in a salt form, it can be converted into a free form or a different salt form by a publicly known method or a modification of the known method.

The DNA encoding the protein of the present invention may be any DNA so long as it contains the base sequence encoding the protein of the present invention described above. Such a DNA may also be any one of genomic DNA, genomic DNA library, cDNA derived from the cells or tissues described above, cDNA library derived from the cells or tissues described above and synthetic DNA. The vector to be used for the library may be any of bacteriophage, plasmid, cosmid, phagemid and the like. In addition, the DNA can be directly amplified by reverse transcriptase polymerase chain reaction (hereinafter abbreviated as RT-PCR) with total RNA or mRNA fraction prepared from the above-described cells or tissues.

Specifically, the DNA encoding the protein of the present invention may be any one of, for example, DNA containing the base sequence represented by SEQ ID NO:2, or any DNA having a base sequence hybridizable to the base sequence represented by SEQ ID NO:2 under high stringent conditions and encoding a protein which has the activities substantially equivalent to those of the protein of the present invention (e.g., a GABA transporter activity, etc.).

Specific examples of the DNA that is hybridizable to the base sequence represented by SEQ ID NO:2 include DNA having at least about 90% homology, preferably at least about 95% homology, and more preferably at least about 98% homology, to the base sequence represented by SEQ ID NO:2.

The hybridization can be carried out by publicly known methods or by a modification thereof, for example, according to the method described in Molecular Cloning, 2nd Ed., J. Sambrook et al., Cold Spring Harbor Lab. Press, (1989). A commercially available library may also be used according to the instructions of the attached manufacturer's protocol. Preferably, the hybridization can be carried out under high stringent conditions.

The high stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration at about 19 mM at a temperature of about 65° C. are most preferred.

More specifically, for the DNA encoding the protein having the amino acid sequence represented by SEQ ID NO:1, there may be employed DNA having the base sequence represented by SEQ ID NO:2, etc.

The DNA encoding the partial peptide of the present invention may be any DNA so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid, phagemid and the like. In addition, the DNA can be directly amplified by reverse transcriptase polymerase chain reaction (hereinafter abbreviated as RT-PCR) with total RNA or mRNA fraction prepared from the above-described cells or tissues Specifically, the DNA encoding the partial peptide of the present invention includes, for example, DNA containing a partial base sequence of the DNA having the base sequence represented by SEQ ID NO:2, or (ii) DNA which has a base sequence hybridizable to the base sequence represented by SEQ ID NO:2 under high stringent conditions and contains a partial base sequence of the DNA encoding the protein having the activities substantially equivalent to those of the protein of the present invention (e.g., a GABA transporter activity, etc.).

Specific examples of the DNA that is hybridizable to the base sequence represented by SEQ ID NO:2 include DNA having at least about 95% homology, preferably at least about 98% homology, to the base sequence represented by SEQ ID NO:2. The hybridization and the high stringent conditions used are those as described above.

For cloning of the DNA that completely encodes the protein or its partial peptide of the present invention (hereinafter collectively referred to as the protein of the present invention), (1) the DNA may be amplified by PCR using synthetic DNA primers containing a part of the base sequence of the protein of the present invention, or (2) the DNA inserted into an appropriate vector can be selected by hybridization with a labeled DNA fragment or synthetic DNA that encodes a part or the entire region of the protein of the present invention, etc. The hybridization can be carried out, for example, according to the method described in Molecular Cloning, 2nd (J. Sambrook et al., Cold Spring Harbor Lab. Press, 1989) or the like. The hybridization may also be performed using commercially available library in accordance with the protocol described in the attached instructions.

Conversion (deletion, addition or substitution) of the base sequence for DNA can be effected by publicly known methods such as the Gapped duplex method or the Kunkel method or modifications thereof, using a publicly known kit available as Mutan™-G or Mutan™-K⁻ (both Takara Shuzo Co., Ltd.).

The cloned DNA encoding the protein of the present invention can be used as it is, or, if desired, after digestion with restriction enzymes or after addition of linkers thereto, depending upon purposes. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the protein of the present invention can be manufactured, for example, by (a) excising the desired DNA fragment from the DNA encoding the protein of the present invention, (b) and then ligating the DNA fragment with an appropriate expression vector downstream a promoter in the expression vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, HIV.LTR promoter, CMV promoter, HSV-TK promoter, etc. Among them, CMV promoter or SRα promoter is preferably used. Where the host is bacteria belonging to the genus *Escherichia*, preferred examples are trp promoter, lac promoter, recA promoter, λPL promoter, lpp promoter, etc. In the case of using bacteria of the genus *Bacillus* as the host, preferred example are SPO1 promoter, SPO2 promoter, penP promoter, etc. When yeast is used as the host, preferred examples are PHO5 promoter, PGK promoter, GAP promoter, ADH promoter, etc. When insect cells are used as the host, preferred examples are polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo, G418 resistance), etc. If necessary, a signal sequence that matches with a host is added to the N-terminus of the protein of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the protein of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus *Bacillus* include *Bacillus subtilis* MI114 (Gene, 24, 255 (1983)), 207-21 (Journal of Biochemistry, 95, 87 (1984)), etc.

Examples of yeast employed are *Saccharomyces cerevisiae* AH22, AH22R⁻, NA87-11A, DKD-5D, 20B-12, *Schizosaccharomyces pombe* NCYC1913, NCYC2036, *Pichia pastoris* KM71, etc.

As insect cells, there may be employed, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc., when the virus is AcNPV; when the virus is BmNPV, *Bombyx mori* N cells (BmN cells), etc. are used. Examples of the Sf cells which can be used are Sf9 cells (ATCC CRL1711) and Sf21 cells (both cells are described in Vaughn, J. L. et al., In Vivo, 13, 213–217 (1977)).

As the insect, for example, a larva of *Bombyx mori* can be used (Maeda et al., Nature, 315, 592 (1985)).

Examples of animal cells include monkey cell COS-7, Vero, Chinese hamster cell CHO (hereinafter abbreviated as CHO cells), dhfr gene deficient Chinese hamster cell CHO (hereinafter abbreviated as CHO (dhfr⁻) cells), mouse L cells, mouse AtT-20, mouse myeloma cells, rat GH 3, human FL cells, HEK293 cells, C127 cells, BALB3T3 cells, Sp-2 cells, etc. Among them, CHO cells, CHO (dhfr⁻) cells, HEK293 cells, LM cells, etc. are preferred.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979).

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55(1988).

Methods for introducing the expression vectors into animal cells include, for example, the calcium phosphate method [Graham, F. L. and van der Eb, A., J. Virology, 52, 456–467 (1973)], the electroporation method [Nuemann, E. et al., EMBO J., 1, 841–845 (1982)], etc.

As described above, transformants transformed with the expression vector containing the DNA encoding the protein of the present invention can be obtained.

For stably expressing the protein of the present invention using animal cells, there is applicable a method of selecting the cells by clone selection in which the aforesaid expression vectors transfected to animal cells are introduced into chromosomes. Specifically, transformants are selected using as an index the selection marker described above. Further by repeated clone selections on the transformants thus obtained using the selection marker, stable animal cell line capable of highly expressing the protein of the present invention can be obtained. Furthermore, when the dhfr gene is used as a selection marker, cultivation can be performed by gradually increasing a level of MTX, resistant cells are selected thereby to amplify the DNA encoding the protein of the present invention in the cells together with the dhfr gene. Thus, the animal cell line of higher expression can be obtained.

The transformant described above is cultivated under conditions that the DNA encoding the protein of the present invention can express, to produce and accumulate the protein of the present invention. Thus, the protein of the present invention or its salts can be produced.

Where the host is bacteria belonging to the genus *Escherichia* or the genus *Bacillus*, the transformant can be appropriately incubated in a liquid medium, which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors, etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431–433, Cold Spring Harbor Laboratory, New York, 1972). If necessary, a chemical such as 3β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary, the culture may be aerated or agitated.

Where the bacteria belonging to the genus *Bacillus* are used as the host, the transformant is cultivated generally at about 30° C. to about 40° C. for about 6 hours to about 24 hours. If necessary, the culture can be aerated or agitated.

Where yeast is used as the host, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), etc. Preferably, pH of the medium is adjusted to about 6 to about 8. The transformant is usually cultivated at about 30° C. to about 40° C. for about 15 hours to about 72 hours and, if necessary, the culture can be aerated or agitated.

As described above, the protein of the present invention can be produced in the cell membrane of the transformant, etc.

The protein of the present invention can be separated and purified from the culture described above by the following procedures.

When the protein of the present invention is extracted from the culture or cells, after cultivation the transformant or cell is collected by a publicly known method and suspended in a appropriate buffer. The transformant or cell is then disrupted by publicly known methods such as ultrasonication, a treatment with lysozyme and/or freeze-thaw cycling, followed by centrifugation, filtration, etc. Thus, the crude extract of the protein of the present invention can be obtained. The buffer used for the procedures may contain a protein modifier such as urea or guanidine hydrochloride, or a surfactant such as Triton X-100™, etc.

The protein of the present invention contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charges such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the protein of the present invention thus obtained is in a free form, it can be converted into the salt by publicly known methods or modifications thereof. On the other hand, when the protein is obtained in the form of a salt, it can be converted into the free form or in the form of a different salt by publicly known methods or modifications thereof.

The protein of the present invention produced by the recombinant can be treated, prior to or after the purification, with an appropriate protein modifying enzyme so that the protein can be appropriately modified to partially remove a polypeptide. Examples of the protein-modifying enzyme include trypsin, chymotrypsin, arginyl endopeptidase, protein kinase, glycosidase and the like.

The thus produced protein of the present invention or salts thereof can be assayed by an enzyme immunoassay using a specific antibody, or the like.

Antibodies to the protein of the present invention, its partial peptide, or salts thereof may be any of polyclonal antibodies and monoclonal antibodies, as long as they are capable of recognizing the protein of the present invention, its partial peptide, or salts thereof.

The antibodies to the protein of the present invention, its partial peptide, or salts thereof (hereinafter merely referred to as the protein of the present invention) may be manufactured by publicly known methods for manufacturing antibodies or antisera, using as antigens the protein of the present invention.
[Preparation of Monoclonal Antibody]
(a) Preparation of Monoclonal Antibody-producing Cells The protein of the present invention is administered to mammal either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and about 2 to about 10 times in total. Examples of the applicable mammals are monkeys, rabbits, dogs, guinea pigs, mice, rats, sheep and goats, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after two to five days from the final immunization and antibody-producing cells contained therein are fused with myeloma cells from homozoic or heterozoic animal to give monoclonal antibody-producing hybridomas. Assay of the antibody titer in antisera may be carried out, for example, by reacting a labeled form of the protein of the present invention, which will be described later, with the antiserum followed by assaying the binding activity of the labeling agent bound to the antibody. The fusion may be carried out, for example, through the known method by Koehler and Milstein (Nature, 256, 495, 1975). Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-a, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to about 40° C., preferably at about 30 to about 37° C. for about 1 to about 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the protein of the present invention as an antigen directly or together with a carrier, adding an anti-immunoglobulin antibody (where mouse cells are used for the cell fusion, anti-mouse immunoglobulin antibody is used) labeled with a radioactive substance or an enzyme, or Protein A, and detecting the monoclonal antibody bound to the solid phase; a method which comprises adding the supernatant of hybridoma to a solid phase adsorbed with an anti-immunoglobulin antibody or Protein A, adding the protein of the present invention labeled with a radioactive substance or an enzyme and detecting the monoclonal antibody bound to the solid phase; and the like.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for hybridoma cultivation (SFM-101, Nissui Seiyaku Co., Ltd.) and the like can be used. The cultivation is carried out generally at 20° C. to 40° C., preferably at about 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.
(b) Purification of Monoclonal Antibody Separation and purification of a monoclonal antibody can be carried out by publicly known methods, such as separation and purification of immunoglobulins (for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc., and dissociating the binding to obtain the antibody.
[Preparation of Polyclonal Antibody]

The polyclonal antibody of the present invention can be manufactured by publicly known methods or modifications thereof. For example, a mammal is immunized with an immunogen (the protein antigen of the present invention) per se, or a complex of immunogen and a carrier protein is formed, and a mammal is immunized with the complex in a manner similar to the method described above for the manufacture of monoclonal antibodies. The product containing the antibody to the protein of the present invention is collected from the immunized animal followed by separation and purification of the antibody.

In the complex of immunogen and carrier protein used to immunize a mammal, the type of carrier protein and the mixing ratio of a carrier to a hapten may be any type and in any ratio, as long as the antibody is efficiently produced to the hapten immunized by crosslinking to the carrier. For example, bovine serum albumin, bovine thyroglobulin or keyhole limpet hemocyanin is coupled to one hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated esters and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon administration, complete Freund's adjuvant or incomplete Freund's adjuvant may be administered. The administration is usually made once approximately every 2 to 6 weeks and about 3 to about 10 times in total.

The polyclonal antibody can be collected from the blood, ascites, etc., preferably from the blood of mammal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The protein of the present invention, the partial peptide, its amides or esters or salts thereof and the DNA encoding the same can be used for preparation of antibodies and antisera; construction of systems for expressing the protein of the present invention; construction of systems for assaying the GABA transporter activity using the expression systems and screening of pharmaceutical candidate compounds; effecting drug design based on the steric structure of GABA transporters; reagents for preparation of probes and PCR primers for gene diagnosis; production of transgenic animals; or pharmaceutical drugs for the gene prophylaxis and gene therapy.

In particular, by using the system assaying the GABA transporter activity using the expression system of the protein of the present invention, a compound that alters the GABA transporter activity specific to human or mammal can be screened, and the compound can be used as an agent for the prevention/treatment of various diseases.

The protein of the present invention, the partial peptide, its amide or ester, or salts thereof (hereinafter sometimes merely referred to as the protein of the present invention), the DNA encoding the protein of the present invention or its partial peptide (hereinafter sometimes merely referred to as the DNA of the present invention) and the cells that express the protein of the present invention and the antibody to the protein of the present invention (hereinafter sometimes merely referred to as the antibody of the present invention) are specifically explained below, with respect to their applications.

(1) Method of Screening the Compound that Alters the Activities of the Protein of the Present Invention Using the protein of the present invention, or by applying the GABA transporter activity assay system using the constructed expression system of the protein of the present invention, the compound (e.g., a peptide, protein, non-peptide compound, synthetic compound, fermentation product, etc.) or its salt that alters the GABA transporter activity of the protein in accordance with the present invention can be efficiently screened.

Such compounds include compounds that potentiate the GABA transporter activity of the protein of the present invention, compounds that inhibit the GABA transporter activity of the protein of the present invention, and the like.

That is, the present invention provides a method of screening a compound or its salt that alters the function (specifically, a GABA transporter activity) of the protein of the present invention, which comprises comparing the case wherein a test compound is contacted with the protein of the present invention, and the case wherein the test compound is not contacted with the protein of the present invention.

More specifically, the present invention provides:

a method of screening which comprises comparing the case wherein a test compound is contacted with the protein of the present invention, and the case wherein the test compound is not contacted with the protein of the present invention;

a method of screening a compound or its salt that alters the function (specifically, a GABA transporter activity) of the protein of the present invention, which comprises comparing the case wherein a test compound is contacted with a cell containing the protein of the present invention, and the case wherein the test compound is not contacted with the cell containing the protein of the present invention; and, a method of screening a compound or its salt that alters the function (specifically, a GABA transporter activity) of the protein of the present invention, which comprises comparing the case wherein a test compound is contacted with the protein of the present invention expressed on a cell membrane of a transformant by incubation of the transformant, and the case wherein the test compound is not contacted with the protein of the present invention expressed on the cell membrane of the transformant by incubation of the transformant.

Before the proteins of the present invention were obtained, for screening a compound that alters, e.g., the GABA transporter activity, first, candidate compounds were obtained using cells or tissues containing a GABA transporter protein from rats or other animals (primary screening), and then, the candidate compounds needed to be examined whether the compounds actually alter the GABA transporter activity (secondary screening). When cells or tissues were directly used, other transporter proteins were also intermingled, and it was practically difficult to screen such a compound to alter the objective GABA transporter activity.

However, for example, using the cell capable of expressing the human-derived protein of the present invention, the primary screening becomes unnecessary, and the compound that alters the GABA transporter activity can be efficiently screened.

The screening method of the present invention is specifically described below.

First, the protein of the present invention used for the screening method of the present invention may be any material so long as it contains the protein of the present invention described above. Preferred are cells containing the protein of the present invention derived from mammalian organs. Since it is very difficult to obtain human-derived organs in particular, however, cells in which the human-derived protein is expressed are suitable for use in the screening.

The cells in which the protein of the present invention is expressed can be constructed by the methods described above, preferably by expressing the DNA of the present invention in mammalian or insect cells. The DNA fragments encoding the objective protein portion include, but are not necessarily limited to, complementary DNA. For example, gene fragments or synthetic DNA may also be used. For introducing DNA fragments encoding the protein of the present invention into host animal cells and efficiently expressing these fragments, it is preferred to insert the DNA fragments downstream the polyhedrin promoter of nuclear polyhedrosis virus (NPV), which is a baculovirus having insect as a host, an SV40-derived promoter, a retrovirus promoter, a metallothionein promoter, a human heat shock promoter, a cytomegalovirus promoter, an SRα promoter or the like. Any cell is usable for expression as long as the protein of the present invention can be surely expressed in the cells, but it is preferred to use cells having a low GABA transporter activity. The amount and quality of the GABA transporter expressed can be determined by publicly known methods. For example, the determination can be made in accordance with the method for assaying the uptake activity of labeled GABA into the cells (The Journal of Biological Chemistry, 267 (29), 21098–21104 (1992)) or by the method for assaying the activity of binding a compound for inhibiting labeled GABA uptake to the cells (Brain Research, 647, 231–241 (1994)).

More specifically, the cells containing the protein of the present invention are first cultured on a multi-well plate, etc. After the medium is replaced with a buffer suitable for uptake of GABA, a test compound and labeled GABA are added, followed by incubation for a given period of time and then washing with a buffer suitable for uptake of GABA. Subsequently, the amount of labeled GABA uptake into the cells is determined so that screening can be effected.

Examples of test compounds include a peptide, a protein, a non-peptide compound, a synthetic compound, a fermentation product, a cell extract, a plant extract, an animal tissue extract and the like. These compounds may be novel compounds or publicly known compounds.

The compounds that inhibit the activity of the protein of the present invention are useful as safe and low-toxic medicaments for, e.g., anxiety, spasm, epilepsy, schizophrenia, cerebrovascular disorders, cerebral palsy, spastic spinal paralysis, spondylosis deformans, spinocerebellar degeneration, spastic paralysis accompanied by multiple sclerosis, tension headache, lumbago, neck, shoulder and arm syndrome, etc.

On the other hand, the compounds that accelerate the activity of the protein of the present invention are useful as safe and low-toxic medicaments for, e.g., dementia including Alzheimer disease.

Since the protein of the present invention also has an osmotic pressure regulating action, the compounds that accelerate or inhibit the activity of the protein of the present invention can thus be used as a diuretic in renal ureterolithiasis, as a medicament for the prevention/treatment of intracranial hypotension in brain abscess, ocular hypotension in glaucoma and cerebral edema, as a regulator of cerebral pressure and ocular hypertensive conditions, as a medicament for the treatment of oliguria, edema intracranial hypertension and intracranial edema, an agent for post-treatment after brain surgery, and as a medicament for the prevention/treatment of oliguria or anuria in acute renal insufficiency.

The screening kit of the present invention comprises the protein of the present invention
Protein-expressing cell (specifically, LM (TK⁻ cell, etc.) used in EXAMPLE 5 later described).

Examples of the screening kit according to the present invention include the following:
[Reagents for Screening]
(1) Buffer for Assay
A buffer for GABA uptake (150 mM NaCl, 20 mM HEPES, 1 mM $CaCl_2$, 10 mM glucose, 5 mM KCl, 1 mM $MgCl_2$, pH was adjusted to 7.4)
(2) [$^3$H]-GABA
(3) Protein Preparation of the Present Invention When the compound or salts thereof obtainable by the screening method or the screening kit of the present invention are used as the pharmaceutical compositions (agents for the prevention/treatment) described above, the pharmaceutical compositions may be prepared in a conventional manner. For example, the compound or its salts may be prepared into tablets, capsules, elixirs, microcapsules, sterile solutions, suspensions, etc.

Since the thus obtained preparations are safe and low toxic, the preparations can be administered to human or mammal (e.g., rat, rabbit, sheep, swine, bovine, cat, dog, monkey, etc.) orally or parenterally.

The dose of the compound or its salt varies depending on, target disease, subject to be administered, route for administration, etc.; when an inhibitor to the protein of the present invention is orally administered for the treatment of, e.g., anxiety, epilepsy, schizophrenia, etc., the inhibitor is normally administered in a dose of about 0.1 mg to about 100 mg, preferably about 1.0 to about 50 mg, more preferably about 1.0 to about 20 mg per day for adult (as 60 kg body weight). In parenteral administration, the single dose of the compound varies depending on subject to be administered, target disease, etc. but for the purpose of treating, e.g., anxiety, epilepsy, schizophrenia, etc., it is advantageous to administer the inhibitor in the form of injection intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.
(1a) Method of Screening the Compound that Alters the GABA Transporter Activity Using the protein of the present invention, or by applying the GABA transporter activity assay system using the constructed expression system of the protein of the present invention together with the GABA transporter activity assay system suitably using the other proteins having a GABA transporter activity (GAT-1, GAT-3, BGT-1, etc.), the compound (e.g., a peptide, protein, non-peptide compound, synthetic compound, fermentation product, etc.) or its salt that alters the GABA transporter activity specific to a particular subtype of the GABA transporter can be efficiently screened by comparing the respective activities.

That is, the present invention provides a method of screening a compound or its salt that promotes or inhibits the GABA transporter activity, which comprises assaying the GABA transporter activity using the protein of the present invention.

Such compounds include the compounds that potentiate the GABA transporter activity of the protein of the present invention but do not potentiate (or do not inhibit) the GABA transporter activity of other subtypes (GAT-1, GAT-3, BTG-1, etc.), the compounds that , the compounds that do not potentiate (or do not inhibit) the GABA transporter activity of the protein of the present invention but potentiate the GABA transporter activity of other subtypes (GAT-1, GAT-3, BTG-1, etc.), and the like.

It is particularly preferred to use the GABA transporter activity assay system using the expression system of the protein of the present invention in combination with the GABA transporter activity assay system using the expression system of GAT-1 or GAT-3 protein.

The GABA transporter activity assay system using other subtypes (GAT-1, GAT-3, BTG-1, etc.) can be constructed as in the GABA transporter activity assay system using the expression system of the protein of the present invention.

The thus obtained compounds that inhibit the GABA transporter activity are useful as safe and low-toxic medicaments for, e.g., anxiety, spasm, epilepsy, schizophrenia, cerebrovascular disorders, cerebral palsy, spastic spinal paralysis, spondylosis deformans, spinocerebellar degeneration, spastic paralysis accompanied by multiple sclerosis, tension headache, lumbago, neck, shoulder and arm syndrome, etc.

On the other hand, the compounds that accelerate the GABA transporter activity are useful as safe and low-toxic medicaments for, e.g., dementia including Alzheimer disease.

Since the protein of the present invention also has an osmotic pressure regulating action, the compounds that accelerate or inhibit the GABA transporter activity can therefore be used as a diuretic in renal ureterolithiasis, as a medicament for the prevention/treatment of intracranial hypotension in brain abscess, ocular hypotension in glaucoma and cerebral edema, as a regulator of cerebral pressure and ocular hypertensive conditions, as a medicament for the treatment of oliguria, edema intracranial hypertension and intracranial edema, an agent for post-treatment after brain surgery, and as a medicament for the prevention/treatment of oliguria or anuria in acute renal insufficiency.

The screening kit of the present invention comprises the protein of the present invention (preferably, the cell capable of expressing the protein of the present invention and other subtypes (GAT-1, GAT-3, BGT-1, etc.) proteins (preferably, other subtypes (GAT-1, GAT-3, BGT-1, etc.) protein-expressing cells (specifically, LM (TK⁻ cell, etc.) used in EXAMPLE 5 later described).

Examples of the screening kit according to the present invention include the following:

[Reagents for Screening]

(1) Buffer for Assay

A buffer for GABA uptake (150 mM NaCl, 20 mM HEPES, 1 mM $CaCl_2$, 10 mM glucose, 5 mM KCl, 1 mM $MgCl_2$, pH was adjusted to 7.4)

(2) [$^3$H]-GABA (3) Protein Preparation of the Invention and Other Subtypes (GAT-1, GAT-3, BGT-1, etc.) Protein Preparations Cells capable of expressing the protein of the present invention and other subtypes (GAT-1, GAT-3, BGT-1, etc.) proteins When the compound or its salts obtainable by the screening method or the screening kit of the present invention are used as the pharmaceutical compositions described above, the compositions may be prepared in a conventional manner. For example, the compound or its salts may be prepared into tablets, capsules, elixirs, microcapsules, sterile solutions, suspensions, etc.

The thus obtained preparations are safe and low toxic, and can be administered to human or mammal (e.g., rat, rabbit, sheep, swine, bovine, cat, dog, monkey, etc.) orally or parenterally.

The dose of the compound or its salt varies depending on, target disease, subject to be administered, route for administration, etc.; when an inhibitor to the protein of the present invention is orally administered for the treatment of, e.g., anxiety, epilepsy, schizophrenia, etc., the inhibitor is normally administered in a dose of about 0.1 mg to about 100 mg, preferably about 1.0 to about 50 mg, more preferably about 1.0 to about 20 mg per day for adult (as 60 kg body weight). In parenteral administration, the single dose of the compound varies depending on subject to be administered, target disease, etc. but for the purpose of treating, e.g., anxiety, epilepsy, schizophrenia, etc., it is advantageous to administer the inhibitor in the form of injection intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

(2) Quantification for the Protein of the Present Invention, its Partial Peptide, or Salts Thereof The antibody of the present is capable of specifically recognizing the protein of the present invention, and can thus be used for quantification of the protein of the present invention in a test sample fluid, in particular, for quantification by sandwich immunoassay. That is, the present invention provides:

(i) a method for quantification of the protein of the present invention or the receptor protein of the present invention in a test sample fluid, which comprises competitively reacting the antibody of the present invention, a test sample fluid and a labeled form of the protein of the present invention, and measuring the ratio of the labeled protein of the present invention bound to said antibody; and, (ii) a method for quantification of the protein of the present invention in a test sample fluid, which comprises reacting a test sample fluid simultaneously or continuously with the antibody of the present invention immobilized on a carrier and a labeled form of the antibody of the present invention, and then assaying the activity of the labeling agent on the insoluble carrier.

In the method (ii) described above, it is preferred that one antibody is capable of recognizing the N-terminal region of the protein of the present invention, while another antibody is capable of recognizing the C-terminal region of the protein of the present invention.

The monoclonal antibody to the protein of the present invention (hereinafter sometimes referred to as the monoclonal antibody of the present invention) may be used to assay the protein of the present invention. Moreover, the protein of the present invention can be detected by means of a tissue staining as well. For these purposes, the antibody molecule per se may be used, or F(ab')$_2$, Fab' or Fab fractions of the antibody molecule may also be used. Any particular limitation should not be posed on the assay method using the antibody to the protein of the present invention; any method may be used so far as it is based on a method in which the amount of antibody, antigen or antibody-antigen complex can be detected by a chemical or a physical means, depending on or corresponding to the amount of antigen (e.g., the amount of the protein of the present invention) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of labels used in the assay method using labeling substances are radioisotopes, enzymes, fluorescent substances, luminescent substances, and the like. Examples of the radioisotope are [$^{125}$I], [$^{131}$I], [$^3$H], [$^{14}$C], etc. Preferred examples of the enzymes are those that are stable and have a high specific activity, which include β-galactosidase, β-glucosidase, alkaline phosphatase, peroxidase and malate dehydrogenase. Examples of the fluorescent substances are fluorescamine, fluorescein isothiocyanate, etc. Examples of the luminescent substances are luminol, luminol derivatives, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding that is conventionally used for immobilization of proteins or enzymes may be used as well. Examples of the carrier include insoluble polysaccharides such as agarose, dextran, cellulose, etc.; synthetic resins such as polystyrene, polyacrylamide, silicone, etc.; glass; etc.

In the sandwich method, a test sample fluid is reacted with an immobilized monoclonal antibody of the present invention (first reaction), then reacted with another labeled monoclonal antibody of the present invention (second reaction) and the activity of the labeling agent on the insoluble carrier is assayed, whereby the amount of the protein of the present invention in the test sample fluid can be quantified. The first and second reactions may be carried out in a reversed order, simultaneously or sequentially with an interval. The type of the labeling agent and the method for immobilization may be performed in a manner similar to those described hereinabove. In the immunoassay by the sandwich method, it is not always necessary that the antibody used for the labeled antibody and for the solid phase should be one type or one species but a mixture of two or more antibodies may also be used for the purpose of improving the measurement sensitivity, etc.

In the method for assaying the protein of the present invention by the sandwich method according to the present invention, antibodies, which binding sites to the protein of the present invention are different from one another, are preferably employed as the monoclonal antibodies of the present invention used for the first and the second reactions. Thus, the antibodies used in the first and the second reactions are those wherein, when the antibody used in the second reaction recognizes the C-terminal region of the protein of the present invention or the receptor protein, the antibody recognizing the site other than the C-terminal regions, e.g., recognizing the N-terminal region, is preferably used in the first reaction.

The monoclonal antibody of the present invention may be used in an assay system other than the sandwich method, such as a competitive method, an immunometric method and a nephrometry. In the competitive method, an antigen in a test sample fluid and a labeled antigen are competitively reacted with an antibody, then the unreacted labeled antigen (F) and the labeled antigen bound to the antibody (B) are separated (B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, a laser nephrometry utilizing laser scattering can be suitably used.

In applying each of those immunoassays to the assay method for the present invention, any special conditions or operations are not required to set forth. The assay system for the protein of the present invention may be constructed in addition to conditions or operations conventionally used for each of the methods, taking the technical consideration of one skilled in the art into account consideration. For the details of such conventional technical means, a variety of reviews, reference books, etc. may be referred to (for example, Hiroshi Irie (ed.): "Radioimmuroassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.)

As described above, the protein of the present invention can be quantified with high sensitivity, using the antibody of the present invention.

(3) Neutralizing Antibody

In the antibody of the present invention, the neutralizing antibody that can bind to the extracellular region of the protein of the present invention and suppress the function (e.g., the GABA transporter activity) of the protein of the present invention may be used as therapeutic/prophylactic agents for anxiety, spasm, epilepsy, schizophrenia, cerebrovascular disorders, cerebral palsy, spastic spinal paralysis, spondylosis deformans, spinocerebellar degeneration, spastic paralysis accompanied by multiple sclerosis, tension headache, lumbago, neck, shoulder and arm syndrome, etc. The antibody of the present invention can be prepared into a pharmaceutical composition solely or together with physiologically acceptable carriers such as an aid for promote its uptake, and the composition may be administered to human or other warm-blooded animal.

(4) Antisense DNA

Antisense DNA that can bind to the DNA of the present invention complementarily and suppress expression of the DNA can suppress the function of the protein or DNA of the present invention, and can thus be used as a therapeutic/prophylactic agent for anxiety, spasm, epilepsy, schizophrenia, cerebrovascular disorders, cerebral palsy, spastic spinal paralysis, spondylosis deformans, spinocerebellar degeneration, spastic paralysis accompanied by multiple sclerosis, tension headache, lumbago, neck, shoulder and arm syndrome, etc.

When the antisense DNA described above is used as the therapeutic/prophylactic agent above, the antisense DNA is administered directly, or the antisense DNA is inserted into an appropriate vector such as retrovirus vector, adenovirus vector, adenovirus-associated virus vector, etc., which may then be administered as it stands, or with a physiologically acceptable carrier to assist its uptake by gene gun or through a catheter such as a catheter with a hydrogel.

As the antisense DNA having a base sequence substantially complementary to the DNA encoding the protein of the present invention or its partial peptide (hereinafter sometimes simply referred to as DNA of the present invention), any antisense DNA is usable as long as it has a base sequence substantially complementary to the DNA of the present invention and has the action capable of suppressing expression of the DNA.

The base sequence substantially complementary to the DNA of the present invention may, for example, be a base sequence having at least about 95% homology, preferably at least about 98% homology, to the full-length base sequence or partial base sequence of the base sequence complementary to the DNA of the present invention (i.e., complementary strand to the DNA of the present invention). Particularly in the entire base sequence of the complementary strand to the DNA of the present invention, an antisense DNA having at least about 95% homology, preferably at least about 98% homology, to the complementary strand of the base sequence which encodes the N-terminal region of the protein or its partial protein of the present invention (e.g., the base sequence around the initiation codon). These antisense DNAs can be synthesized using a publicly known DNA synthesizer, etc.

(5) Preparation of Non-human Animal Bearing the DNA Encoding the Protein of the Present Invention Transgenic non-human mammals capable of expressing the protein of the present invention can be prepared using the DNA of the present invention. Examples of the non-human mammals include mammals (e.g., rats, mice, rabbits, sheep, swine, bovine, cats, dogs, monkeys and the like) (hereinafter referred to as animal). Above all, preferred are mice and rats.

To introduce the DNA of the present invention to a target animal, it is generally advantageous to employ the DNA in a gene construct ligated downstream a promoter capable of expressing the DNA in an animal cell. For example, when the mouse-derived DNA of the present invention is transferred, for example, the gene construct, in which the DNA is ligated downstream various promoters capable of expressing the DNA of the present invention derived from an animal that is highly homologous to the DNA of the present invention, is microinjected to mouse fertilized ova. Thus, the DNA-transferred animal capable of producing a high level of the protein of the present invention can be prepared. Examples of the promoters that can be used are a virus-derived promoter and a ubiquitous expression promoter such as metallothionein.

The transfer of the DNA of the present invention at the fertilized egg cell stage secures the presence of DNA in all germ and somatic cells in the target animal. The presence of the protein of the present invention in the germ cells in the DNA-transferred animal means that all germ and somatic cells contain the protein of the present invention in all progenies of the animal. The progenies of the animal that took over the gene contain the protein of the present invention in all germ and somatic cells.

The transgenic animal to which the DNA of the present invention has been transferred can be subjected to a mating and a breeding for generations under common breeding circumstance, as the DNA-carrying animal, after confirming that the gene can be stably retained. Moreover, male and female animals having the desired DNA are mated to give a homozygote having the transduced gene in both homologous chromosomes and then the male and female animals are mated so that such breeding for generations that progenies contain the DNA can be performed.

The transgenic animal to which the DNA of the present invention has been transferred is useful as the animal for screening of drugs that act on the protein of the present invention, since the protein of the present invention is abundantly expressed.

The transgenic animal to which the DNA of the present invention has been transferred can also be used as the cell sources for tissue culture. The protein of the present invention can be analyzed by, for example, direct analysis of the DNA or RNA in tissues of the DNA-transferred mice of the present invention, or by analysis of tissues containing the protein of the present invention expressed from the gene. Cells from tissues containing the protein of the present invention are cultured by the standard tissue culture technique. Using these cells, the function of the cells from tissues that are generally difficult to culture, for example, cells derived from the brain and peripheral tissues can be studied Using these cells it is also possible to screen pharmaceuticals, for example, that increase the function of various tissues. Where a highly expressing cell line is available, the protein of the present invention can be isolated and purified from the cell line.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |

-continued

| | |
|---|---|
| Gln | glutamine |
| pGlu | pyroglutamic acid |
| Me | methyl group |
| Et | ethyl group |
| Bu | butyl group |
| Ph | phenyl group |
| TC | thiazolidine-4(R)-carboxamide group |

Substituents, protecting groups, and reagents frequently used in the specification are denoted by the codes below.

| | |
|---|---|
| Tos | p-toluenesulfonyl |
| CHO | formyl |
| Bzl | benzyl |
| $Cl_2Bzl$ | 2,6-dichlorobenzyl |
| Bom | benzyloxymethyl |
| Z | benzyloxycarbonyl |
| Cl—Z | 2-chlorobenzyloxycarbonyl |
| Br—Z | 2-bromobenzyloxycarbonyl |
| Boc | t-butoxycarbonyl |
| DNP | dinitrophenol |
| Trt | trityl |
| Bum | t-butoxymethyl |
| Fmoc | N-9-fluorenylmethoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboximide |
| DCC | N,N'-dichlorohexylcarbodiimide |

The sequence identification numbers (SEQ ID NO:) in the sequence listing of the specification indicates the following sequence, respectively.

[SEQ ID NO: 1]
The sequence shows the amino acid sequence of the protein of the present invention encoded by human GAT2 gene, obtained by EXAMPLE 3 below.

[SEQ ID NO: 2]
The sequence shows the base sequence encoded by human GAT2 gene, obtained by EXAMPLE 3 below.

[SEQ ID NO: 3]
The sequence shows the base sequence of primer HGA2U used in EXAMPLE 1 below.

[SEQ ID NO: 4]
The sequence shows the base sequence of primer HGA2L used in EXAMPLE 1 below.

[SEQ ID NO: 5]
The sequence shows the base sequence of primer HGA2-198L used in EXAMPLE 2 below.

[SEQ ID NO: 6]
The sequence shows the base sequence of primer HGA2-247L used in EXAMPLE 2 below.

[SEQ ID NO: 7]
The sequence shows the base sequence of primer HGA2-1665U used in EXAMPLE 2 below.

[SEQ ID NO: 8]
The sequence shows the base sequence of primer HGA2-1613U used in EXAMPLE 2 below.

[SEQ ID NO: 9]
The sequence shows the base sequence of primer AP-1 used in EXAMPLE 2 below.

[SEQ ID NO: 10]
The sequence shows the base sequence of primer AP-2 used in EXAMPLE 2 below.

[SEQ ID NO: 11]
The sequence shows the base sequence of primer HGA2-U2 used in EXAMPLE 3 below.

[SEQ ID NO: 12]
The sequence shows the base sequence of primer HGA2-L2 used in EXAMPLE 3 below.

Transformant *Escherichia coli* DH5α/pMCMV-hGAT2 bearing the plasmid pMCMV-hGAT2 obtained in EXAMPLE 4 later described was on deposit with the Ministry of International Trade and Industry, Agency of Industrial Science and Technology, National Institute of Bioscience and Human Technology (NIBH) at 1-1-3, Higashi, Tsukuba-shi, Ibaraki, Japan, as the Accession Number FERM BP-6739 on Jun. 2, 1999 and with Institute for Fermentation, Osaka (IFO) at 2-17-85, Juso Honcho, Osaka-shi, Osaka, Japan, as the Accession Number-IFO 16286 on Apr. 28, 1999.

EXAMPLES

Genetic manipulation described in the following EXAMPLES was performed in accordance with methods described in the textbook (Maniatis et al., Molecular Cloning, Cold Spring Harbor Laboratory, 1989) or by the procedures described in the protocols attached to reagents.

Example 1

Partial Cloning of Human GAT2 Gene

Using as a template human retina-derived cDNA (Toyobo, QUICK-Clone cDNA), partial cloning of human GAT2 gene was carried out by PCR using the primer set below prepared with reference to the base sequence of rat GAT2 gene reported by Borden et al. (J. Biol. Chem., 267, 21098–21104 (1992)).

HGA2U: 5'-GGT GGG ATG GAT AAC AGG GTC TCG GGA ACG [SEQ ID NO:3]

HGA2L: 5'-CCC TAG CAG TTA GAC TCC AGT TCT GTG AGC [SEQ ID NO:4]

The PCR procedure was performed by a Hot Start method using AmpliWax PCR Gem 100 (TAKARA SHUZO CO., LTD.). First, 2 ml of 10×LA PCR Buffer, 3 ml of 2.5 mM dNTP solution, 2 ml of 25 mM $MgCl_2$, 2.5 ml each of primer solutions ([SEQ ID NO:3] and [SEQ ID NO:4]) and 8 ml of sterilized distilled water were mixed to obtain a bottom layer solution mixture. One milliliter of human retina cDNA (1 ng/ml) as a template, 3 ml of 10×LA PCR Buffer, 1 ml of 2.5 mM dNTP solution, 3 ml of 25 mM $MgCl_2$, 0.5 ml of TaKaRa LA Taq DNA polymerase (TAKARA SHUZO CO., LTD.) and 21.5 ml of sterilized distilled water were mixed to obtain a top layer solution mixture. The bottom solution mixture thus prepared received one unit of AmpliWax PCR Gem 100 (TAKARA SHUZO CO., LTD.), and was treated at 70° C. for 5 minutes and then in ice for 5 minutes. Thereafter, the top layer solution mixture was added to prepare the reaction mixture of PCR. A tube containing the reaction mixture was set on a thermal cycler (Perkin Elmer) and treated at 95° C. for 2 minutes. After repeating the cycle of 98° C. for 10 seconds followed by 60° C. for 30 seconds and then 72° C. for 2 minutes 45 times, the tube was further treated at 72° C. for 8 minutes. The PCR product thus obtained was subjected to electrophoresis on agarose gel (1%) to recover 1.8 kb DNA fragment containing GAT2 gene from the gel. Then, the fragment was inserted into pT7 Blue vector (TAKARA SHUZO CO., LTD.) to obtain a plasmid designated as pT7-GAT2.

Confirmation of the base sequence for the PCR fragment part of pT7-GAT2 shows that the base sequence contained a sequence similar to rat-derived CAT2 gene.

Example 2

Cloning of Human GAT2 Gene at the 5' and 3' Regions

The 5' and 3' regions in the sequence of the PCR fragment obtained in EXAMPLE 1 are sequences of rat GAT2 gene.

Thus, for cloning human GAT2 gene at the 5' and 3' regions, the cloning was carried out using as templates human retina- and kidney-derived cDNAs (Toyobo, Marathon Ready cDNA), by nested PCR procedures of a RACE (Rapid Amplification of cDNA End) method using the following specific primer set prepared with reference to the base sequence of pT7-GAT2 gene:

HGA2-198L:
    5'-GCA CCT CCC CCA TTT TTG TAG CAG [SEQ ID NO:5]
HGA2-247L:
    5'-GAC AGG AAT GCC ACA GGT AAA GAG [SEQ ID NO:6]
HGA2-1665U:
    5'-CTC TAC AGA CTC GGA ACC CTC AAG [SEQ ID NO:7]
HGA2-1613U:
    5'-CCT GGG CTG GCT CCT GGC TCT GTC [SEQ ID NO:8] and the primer set attached to Marathon Ready cDNA:
AP-1:
    5'-CCA TCC TAA TAC GAC TCA CTA TAG GGC [SEQ ID NO:9]
AP-2:
    5'-ACT CAC TAT AGG GCT CGA GCG GC [SEQ ID NO:10]

The first PCR procedure for the 5' region was performed by a Hot Start method using AmpliWax PCR Gem 100 (TAKARA SHUZO CO., LTD.). A bottom layer solution mixture was prepared by mixing 2 ml of 10× pyrobest DNA polymerase Buffer, 3 ml of 2.5 mM dNTP solution, 1 ml each of primer solutions (HGA2-247L [SEQ ID NO:6] and AP-1 [SEQ ID NO:9]) and 13 ml of sterilized distilled water. Five milliliters of human retina- and kidney-derived cDNAs as a template, 3 ml of 10× pyrobest DNA polymerase Buffer, 1 ml of 2.5 mM dNTP solution, 0.5 ml of pyrobest DNA polymerase (TAKARA SHUZO CO., LTD.) and 20.5 ml of sterilized distilled water were mixed to obtain a top layer solution mixture. The bottom solution mixture thus prepared received one unit of AmpliWax PCR Gem 100 (TAKARA SHUZO CO., LTD.), and was treated at 70° C. for 5 minutes and then in ice for 5 minutes. Thereafter, the top layer solution mixture was added to prepare the reaction mixture of PCR. A tube charged with the reaction mixture was set on a thermal cycler (Perkin Elmer) and treated at 94° C. for 2 minutes. The cycle of 94° C. for 5 seconds and 72° C. for 3 minutes was repeated 5 times, then the cycle of 94° C. for 5 seconds and 70° C. for 3 minutes 5 times, followed by the cycle of 94° C. for 5 seconds and then 68° C. for 3 minutes 25 times. Then, the nested PCR was performed using the PCR product obtained as a template. That is, 2 ml of 10×LA PCR Buffer, 3 ml of 2.5 mM dNTP solution, 2 ml of 25 mM MgCl$_2$, 1 ml each of primer solutions (HGA2-198L [SEQ ID NO:5] and AP-2 [SEQ ID NO:10]) and 11 ml of sterilized distilled water were mixed to obtain a bottom layer solution mixture. One milliliter of the PCR products of HGA2-247L and AP-1 at the 5' region as templates, 3 ml of 10×LA PCR Buffer, 1 ml of 2.5 mM dNTP solution, 3 ml of 25 mM MgCl$_2$, 0.5 ml of TaKaRa LA Taq DNA polymerase (TAKARA SHUZO CO., LTD.) and 21.5 ml of sterilized distilled water were mixed to obtain a top layer solution mixture. The bottom solution mixture thus prepared received one unit of AmpliWax PCR Gem 100 (TAKARA SHUZO CO., LTD.), and was treated at 70° C. for 5 minutes and then in ice for 5 minutes. Thereafter, the top layer solution mixture was added to prepare the reaction mixture of PCR. A tube charged with the reaction mixture was set on a thermal cycler (Perkin Elmer) and treated at 94° C. for 2 minutes.

The cycle of 94° C. for 5 seconds and 72° C. for 3 minutes was repeated 5 times, then the cycle of 94° C. for 5 seconds and 70° C. for 3 minutes 5 times, followed by the cycle of 94° C. for 5 seconds and then 68° C. for 3 minutes 25 times.

The first PCR procedure for the 3' region was performed by a Hot Start method using AmpliWax PCR Gem 100 (TAKARA SHUZO CO., LTD.). A bottom layer solution mixture was prepared by mixing 2 ml of 10× pyrobest DNA polymerase Buffer, 3 ml of 2.5 mM dNTP solution, 1 ml each of primer solutions (HGA2-1613U [SEQ ID NO:8] and AP-1 [SEQ ID NO:9]) and 13 ml of sterilized distilled water. Five milliliters of human retina- and kidney-derived cDNAs as a template, 3 ml of 10× pyrobest DNA polymerase Buffer, 1 ml of 2.5 mM dNTP solution, 0.5 ml of pyrobest DNA polymerase (TAKARA SHUZO CO., LTD.) and 20.5 ml of sterilized distilled water were mixed to obtain a top layer solution mixture. The bottom solution mixture thus prepared received one unit of AmpliWax PCR Gem 100 (TAKARA SHUZO CO., LTD.), and was treated at 70° C. for 5 minutes and then in ice for 5 minutes. Thereafter, the top layer solution mixture was added to prepare the reaction mixture of PCR. A tube charged with the reaction mixture was set on a thermal cycler (Perkin Elmer) and treated at 94° C. for 2 minutes. The cycle of 94° C. for 5 seconds and 72° C. for 3 minutes was repeated 5 times, then the cycle of 94° C. for 5 seconds and 70° C. for 3 minutes 5 times, followed by the cycle of 94° C. for 5 seconds and then 68° C. for 3 minutes 25 times. Then, the nested PCR was performed using the PCR product obtained as a template. That is, 2 ml of 10× pyrobest DNA polymerase Buffer, 3 ml of 2.5 mM dNTP solution, 1 ml each of primer solutions (HGA2-1665U [SEQ ID NO:7] and AP-2 [SEQ ID NO:10]) and 13 ml of sterilized distilled water were mixed to obtain a bottom layer solution mixture. One milliliter of the PCR products of HGA2-1613U and AP-1 at the 3' region as templates, 3 ml of 10× pyrobest DNA polymerase Buffer, 1 ml of 2.5 mM dNTP solution, 0.5 ml of pyrobest DNA polymerase (TAKARA SHUZO CO., LTD.) and 24.5 ml of sterilized distilled water were mixed to obtain a top layer solution mixture. The bottom solution mixture thus prepared received one unit of AmpliWax PCR Gem 100 (TAKARA SHUZO CO., LTD.), and was treated at 70° C. for 5 minutes and then in ice for 5 minutes. Thereafter, the top layer solution mixture was added to prepare the reaction mixture of PCR. A tube charged with the reaction mixture was set on a thermal cycler (Perkin Elmer) and treated at 94° C. for 2 minutes. The cycle of 94° C. for 5 seconds and 72° C. for 3 minutes was repeated 5 times, then the cycle of 94° C. for 5 seconds and 70° C. for 3 minutes 5 times, followed by the cycle of 94° C. for 5 seconds and then 68° C. for 3 minutes 25 times.

Direct sequencing of the respective PCR products thus obtained shows that the products contained sequences similar to rat-derived GAT2 gene at the 5' and 3' regions.

Example 3

Cloning of the Full-length of Human GAT2 Gene

Using three different templates of human kidney QUICK-Clone cDNA (Toyobo) and human retina and kidney Mara thon Ready cDNAs (Toyobo), cloning of the full-length human GAT2 gene was carried out by PCR using the specific primer set below prepared with reference to the base sequences of 5' and 3' regions obtained in EXAMPLE 2.
HGA2-U2:
5'-GGC AGC GCT AGC AGG TCT GGC AGC AGC TTC ACT AAG [SEQ ID NO:11]
HGA2-L2:
5'-TCA CCA GTC GAC GGC ACA CAG GCA CCA TCC AAG GGC [SEQ ID NO:12]

The PCR procedure was performed by a Hot Start method using AmpliWax PCR Gem 100 (TAKARA SHUZO Co., LTD.). When human kidney QUICK-Clone cDNA (Toyobo) was used as a template, a bottom layer solution mixture was prepared by mixing 2 ml of 10× pyrobest DNA polymerase Buffer, 3 ml of 2.5 mM dNTP solution, 1 ml each of primer solutions ([SEQ ID NO:11] and [SEQ ID NO:12]) and 13 ml of sterilized distilled water. One milliliter of the template, 3 ml of 10× pyrobest DNA polymerase Buffer, 1 ml of 2.5 mM dNTP solution, 0.5 ml of pyrobest DNA polymerase (TAKARA SHUZO CO., LTD.) and 24.5 ml of sterilized distilled water were mixed to obtain a top layer solution mixture. The bottom solution mixture thus prepared received one unit of Ampliwax PCR Gem 100 (TAKARA SHUZO CO., LTD.), and was treated at 70° C. for 5 minutes and then in ice for 5 minutes. Thereafter, the top layer solution mixture was added to prepare the reaction mixture of PCR. When human retina- and kidney Marathon Ready cDNAs (Toyobo) were used as templates, a bottom layer solution mixture was prepared by mixing 2 ml of 10× pyrobest DNA polymerase Buffer, 3 ml of 2.5 mM dNTP solution, 1 ml each of the primer solutions and 13 ml of sterilized distilled water. Five milliliters of the template, 3 ml of 10× pyrobest DNA polymerase Buffer, 1 ml of 2.5 mM dNTP solution, 0.5 ml of pyrobest DNA polymerase (TAKARA SHUZO CO., LTD.) and 20.5 ml of sterilized distilled water were mixed to obtain a top layer solution mixture. The bottom solution mixture thus prepared received one unit of AmpliWax PCR Gem 100 (TAKARA SHUZO CO., LTD.), and was treated at 70° C. for 5 minutes and then in ice for 5 minutes. Thereafter, the top layer solution mixture was added to prepare the reaction mixture of PCR. A tube charged with the reaction mixture was set on a thermal cycler (Perkin Elmer) and treated at 95° C. for 2 minutes. The cycle of 98° C. for 10 seconds, 60° C. for 30 seconds and 72° C. for 2 minutes was repeated 45 times, then the mixture was treated at 72° C. for 8 minutes. The respective PCR products thus obtained were subjected to electrophoresis on agarose gel (1%) to recover 1.8 kb DNA fragment containing human GAT2 gene from the gel. Then, the fragment was inserted into pT7 Blue vector (TAKARA SHUZO CO., LTD.) to produce pT7-hGAT2 No. 1-11 derived from human kidney QUICK-Clone cDNA, pT7-hGAT2 No. 3-6 derived from human kidney Marathon Ready cDNA, and pT7-hGAT2 No. 4-13 derived from human retina Marathon Ready cDNA.

Since the base sequences for the PCR fragment parts derived from the three different templates all coincided with each other, it was confirmed that human GAT2 gene [SEQ ID NO:2] was acquired.

Example 4

Preparation of Plasmid for Human GAT 2 Expression

By ligating 5.6 Kb NheI-SalI fragment from plasmid pMCMVneo with 1.8 Kb NheI-SalI fragment bearing human GAT2 gene of plasmid pT7-hGAT2 No. 4-13, plasmid pMCMV-hGAT2 was produced.

Using plasmid pMCMV-hGAT2, *Escherichia coli* DH5α strain was transfected to acquire *Escherichia coli* DH5α/pMCMV-hGAT2.

Example 5

Introduction of Human GAT2-expressing Plasmid into LM(TK⁻) Cell and Acquisition of the Expressed Cell A LM(TK⁻) cell cultured in a 750 ml tissue culture flask (Corning) containing DMEM medium (Lifetech Oriental) supplemented with 10% fetal bovine serum (Lifetech Oriental) was scraped by treating with 0.5 g/L trypsin-0.2 g/L EDTA (Lifetech Oriental). The cell was washed with PBS (Lifetech Oriental), centrifuged (1000 rpm, 5 minutes) and then suspended in PBS. Subsequently, a DNA was introduced into the cell under the conditions shown below using GENE PULSER (Bio-Rad Laboratories). That is, a cuvette having a 0.4 cm gap received $8 \times 10^6$ cells and 10 mg of plasmid pMCMV-hGAT2 for expression and was then subjected to electroporation at the voltage of 0.25 kV under the capacitance of 960 mF. Subsequently, the cell was transferred to a DMEM medium containing 10% fetal bovine serum and cultured for 24 hours. Thereafter, the cell was scraped again, centrifuged, and then suspended in DMEM medium containing 10% fetal bovine serum supplemented with 500 mg/ml of GENETICIN (Lifetech Oriental) and diluted to a level of $10^4$ cells/ml upon inoculation onto a 96-well plate (Becton-Dickinson), followed by incubation in a carbonate gas incubator at 37° C. Thus, a GENETICIN-resistant transformant was acquired.

Figure 2:
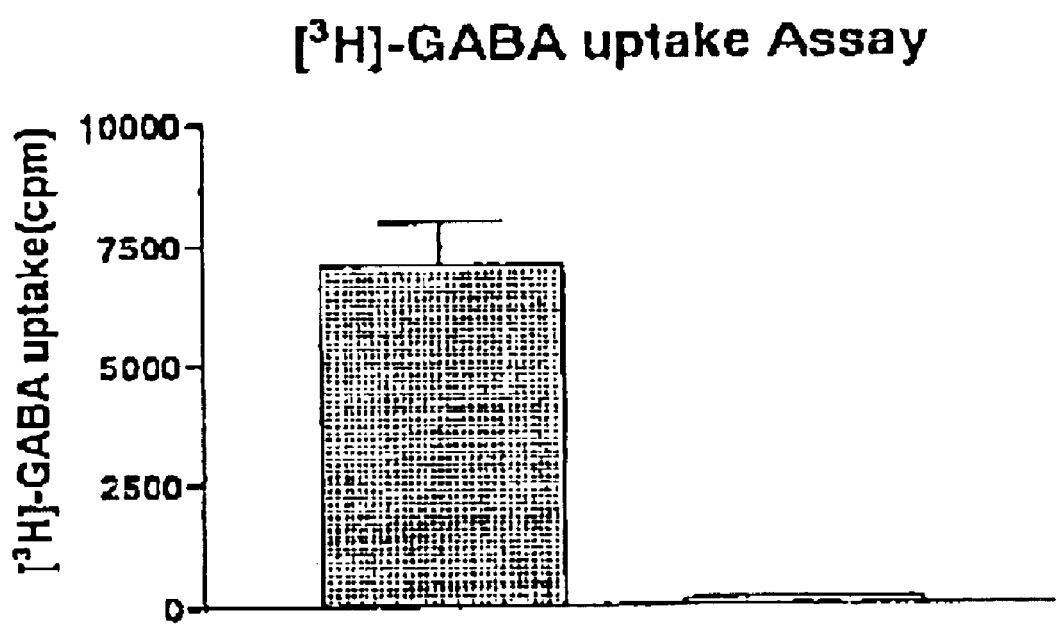
FIG. 2 shows the results of increased amounts of labeled GABA uptake assayed after adding [$^3$H]-GABA to hGAT2/LM(TK$^-$) cells where the protein of the present invention was expressed, in a buffer containing sodium ions and chlorine ions. In the left graph, hGAT2/LM(TK$^-$) designates the LM(TK$^-$) cell wherein the human-derived protein of the present invention was expressed, and in the right graph, Mock/LM(TK$^-$) designates the LM(TK$^-$) cell inserted with plasmid pMCMVneo. The numerical value on the left side denotes the assay results of amounts of labeled GABA uptake measured after adding 50 nM [$^3$H]-GABA to hGAT2/LM(TK$^-$) cells where the protein of the present invention was expressed, in a buffer containing sodium ions and chlorine ions. The data is shown as a mean value ± standard error.

Subsequently, GAT2 expression was confirmed by the following procedures. That is, after the transformant cell line thus obtained was cultured in a 96-well plate (Corning), the medium was replaced by GABA uptake Buffer (150 mM NaCl, 20 mM HEPES, 1 mM $CaCl_2$, 10 mM Glucose, 5 mM KCl, 1 mM $MgCl_2$; pH was adjusted to 7.4) and then 50 nM [$^3$H]-GABA was added thereby to screen a cell line in which the 1[$^3$H]-GABA uptake was induced, i.e., hGAT2/LM (TK⁻) (FIG. 2).

INDUSTRIAL APPLICABILITY

The protein or its salt, the partial protein, its amide or ester, or salts thereof, and DNA encoding the same can be employed for obtaining antibodies and antisera, constructing the expression system of the protein of the present invention, for constructing the assay system for the GABA transporter activity and screening medicament candidate compounds using the expression system, for making drug design based on the steric structure of GABA transporters, as agents for producing probes or PCR primers in gene diagnosis, for preparing transgenic animals or as pharmaceutical compositions for the prevention/treatment of gene, etc.

What is claimed is:

1. An isolated protein which has GABA transporter activity and contains an amino acid sequence, which has at least 95% sequence identity to the amino acid sequence represented by SEQ ID No: 1, or a salt thereof.

2. A kit for screening a compound or its salt that promotes or inhibits a GABA transporter activity, comprising the protein according to claim 1, its amide or ester, or a salt thereof.

3. A kit for screening a compound or its salt that promotes or inhibits a GABA transporter activity of the protein according to claim 1, its amide or ester, or a salt thereof, comprising the protein or its salt according to claim 1, its amide or ester, or a salt thereof.

4. An isolated protein which has a GABA transporter activity and contains an amino acid sequence represented by SEQ ID No: 1, or a salt thereof.

5. A kit for screening a compound or its salt that promotes of inhibits a GABA transporter activity, comprising the protein according to claim 4, its amide or ester, or a salt thereof.

6. A kit for screening a compound or its salt that promotes or inhibits a GABA transporter activity of the protein according to claim 4, its amide or ester, or a salt thereof, comprising the protein or its salt according to claim 4, its amide or ester, or a salt thereof.

* * * * *

SEQUENCE LISTING

<160> NUMBER OF SEQ ID NOS: 12

<210> SEQ ID NO 1
<211> LENGTH: 602
<212> TYPE: PRT
<213> ORGANISM: Human

<400> SEQUENCE: 1

```
Met Asp Ser Arg Val Ser Gly Thr Thr Ser Asn Gly Glu Thr Lys Pro
 1               5                  10                  15

Val Tyr Pro Val Met Glu Lys Lys Glu Asp Gly Thr Leu Glu Arg
                20                  25                  30

Gly His Trp Asn Asn Lys Met Glu Phe Val Leu Ser Val Ala Gly Glu
                35                  40                  45

Ile Ile Gly Leu Gly Asn Val Trp Arg Phe Pro Tyr Leu Cys Tyr Lys
        50                  55                  60

Asn Gly Gly Gly Ala Phe Phe Ile Pro Tyr Leu Val Phe Leu Phe Thr
65                  70                  75                  80

Cys Gly Ile Pro Val Phe Leu Leu Glu Thr Ala Leu Gly Gln Tyr Thr
                85                  90                  95

Ser Gln Gly Gly Val Thr Ala Trp Arg Lys Ile Cys Pro Ile Phe Glu
                100                 105                 110

Gly Ile Gly Tyr Ala Ser Gln Met Ile Val Ile Leu Leu Asn Val Tyr
            115                 120                 125

Tyr Ile Ile Val Leu Ala Trp Ala Leu Phe Tyr Leu Phe Ser Ser Phe
    130                 135                 140

Thr Ile Asp Leu Pro Trp Gly Cys Tyr His Glu Trp Asn Thr Glu
145                 150                 155                 160

His Cys Met Glu Phe Gln Lys Thr Asn Gly Ser Leu Asn Gly Thr Ser
                165                 170                 175

Glu Asn Ala Thr Ser Pro Val Ile Glu Phe Trp Glu Arg Arg Val Leu
            180                 185                 190

Lys Ile Ser Asp Gly Ile Gln His Leu Gly Ala Leu Arg Trp Glu Leu
    195                 200                 205

Ala Leu Cys Leu Leu Leu Ala Trp Val Ile Cys Tyr Phe Cys Ile Trp
210                 215                 220

Lys Gly Val Lys Ser Thr Gly Lys Val Val Tyr Phe Thr Ala Thr Phe
225                 230                 235                 240

Pro Tyr Leu Met Leu Val Val Leu Leu Ile Arg Gly Val Thr Leu Pro
                245                 250                 255

Gly Ala Ala Gln Gly Ile Gln Phe Tyr Leu Tyr Pro Asn Leu Thr Arg
            260                 265                 270

Leu Trp Asp Pro Gln Val Trp Met Asp Ala Gly Thr Gln Ile Phe Phe
    275                 280                 285

Ser Phe Ala Ile Cys Leu Gly Cys Leu Thr Ala Leu Gly Ser Tyr Asn
290                 295                 300

Lys Tyr His Asn Asn Cys Tyr Arg Asp Cys Ile Ala Leu Cys Phe Leu
305                 310                 315                 320

Asn Ser Gly Thr Ser Phe Val Ala Gly Phe Ala Ile Phe Ser Ile Leu
                325                 330                 335

Gly Phe Met Ser Gln Glu Gln Gly Val Pro Ile Ser Glu Val Ala Glu
            340                 345                 350

Ser Gly Pro Gly Leu Ala Phe Ile Ala Tyr Pro Arg Ala Val Val Met
```

```
                    355                 360                 365
Leu Pro Phe Ser Pro Leu Trp Ala Cys Cys Phe Phe Met Val Val
        370                 375                 380
Leu Leu Gly Leu Asp Ser Gln Phe Val Cys Val Glu Ser Leu Val Thr
385                 390                 395                 400
Ala Leu Val Asp Met Tyr Pro His Val Phe Arg Lys Lys Asn Arg Arg
                405                 410                 415
Glu Val Leu Ile Leu Gly Val Ser Val Ser Phe Leu Val Gly Leu
            420                 425                 430
Ile Met Leu Thr Glu Gly Gly Met Tyr Val Phe Gln Leu Phe Asp Tyr
        435                 440                 445
Tyr Ala Ala Ser Gly Met Cys Leu Leu Phe Val Ala Ile Phe Glu Ser
450                 455                 460
Leu Cys Val Ala Trp Val Tyr Gly Ala Lys Arg Phe Tyr Asp Asn Ile
465                 470                 475                 480
Glu Asp Met Ile Gly Tyr Arg Pro Trp Pro Leu Ile Lys Tyr Cys Trp
                485                 490                 495
Leu Phe Leu Thr Pro Ala Val Cys Thr Ala Thr Phe Leu Phe Ser Leu
            500                 505                 510
Ile Lys Tyr Thr Pro Leu Thr Tyr Asn Lys Lys Tyr Thr Tyr Pro Trp
            515                 520                 525
Trp Gly Asp Ala Leu Gly Trp Leu Leu Ala Leu Ser Ser Met Val Cys
        530                 535                 540
Ile Pro Ala Trp Ser Leu Tyr Arg Leu Gly Thr Leu Lys Gly Pro Phe
545                 550                 555                 560
Arg Glu Arg Ile Arg Gln Leu Met Cys Pro Ala Glu Asp Leu Pro Gln
                565                 570                 575
Arg Asn Pro Ala Gly Pro Ser Ala Pro Ala Thr Pro Arg Thr Ser Leu
            580                 585                 590
Leu Arg Leu Thr Glu Leu Glu Ser His Cys
        595                 600

<210> SEQ ID NO 2
<211> LENGTH: 1806
<212> TYPE: DNA
<213> ORGANISM: Human

<400> SEQUENCE: 2
atggatagca gggtctcagg cacaaccagt aatggagaga caaaaccagt gtatccagtc      60
atggaaaaga aggaggaaga tggcaccctg agcgggggc actggaacaa caagatggag     120
tttgtgctgt cagtggctgg ggagatcatt ggcttaggca cgtctggag gtttccctat     180 ctctgctaca aaaatggggg aggtgccttc ttcatcccct acctcgtctt cctctttacc     240
tgtggcattc ctgtcttcct tctggagaca gcactaggcc agtacactag ccagggaggc     300
gtcacagcct ggaggaagat ctgccccatc tttgagggca ttggctatgc ctcccagatg     360
atcgtcatcc tcctcaacgt ctactacatc attgtgttgg cctgggccct gttctacctc     420
ttcagcagct tcaccatcga cctgccctgg ggcggctgct accatgagtg gaacacagaa     480
cactgtatgg agttccagaa gaccaacggc tccctgaatg gtacctctga aatgccacc      540 tctcctgtca tcgagttctg ggagcggcgg gtcttgaaga tctctgatgg gatccagcac     600 ctggggccc tgcgctggga gctggctctg tgcctcctgc tggcctgggt catctgctac     660
ttctgcatct ggaaggggt gaagtccaca ggcaaggtgg tgtacttcac ggccacattt     720
```

-continued

| | |
|---|---|
| ccttacctca tgctggtggt cctgttaatt cgagggtga cgttgcctgg ggcagcccaa | 780 |
| ggaattcagt tttacctgta cccaaacctc acgcgtctgt gggatcccca ggtgtggatg | 840 |
| gatgcaggca cccagatatt cttctccttc gccatctgtc ttgggtgcct gacagccctg | 900 |
| ggcagctaca acaagtacca caacaactgc tacagggact gcatcgccct ctgcttcctc | 960 |
| aacagcggca ccagctttgt ggccggcttt gccatcttct ccatcctggg cttcatgtct | 1020 |
| caggagcagg gggtgcccat ttctgaggtg gccgagtcag gccctggcct ggctttcatc | 1080 |
| gcttacccgc gggctgtggt gatgctgccc ttctctcctc tctgggcctg ctgtttcttc | 1140 |
| ttcatggtcg ttctcctggg actggatagc cagtttgtgt gtgtagaaag cctggtgaca | 1200 |
| gcgctggtgg acatgtaccc tcacgtgttc cgcaagaaga accggaggga agtcctcatc | 1260 |
| cttggagtat ctgtcgtctc cttccttgtg ggctgatca tgctcacaga gggcggaatg | 1320 |
| tacgtgttcc agctctttga ctactatgcg gccagtggca tgtgcctcct gttcgtggcc | 1380 |
| atcttcgagt ccctctgtgt ggcttgggtt tacggagcca agcgcttcta cgacaacatc | 1440 |
| gaagacatga ttgggtacag gccatggcct cttatcaaat actgttggct cttcctcaca | 1500 |
| ccagctgtgt gcacagccac ctttctcttc tccctgataa agtacactcc gctgacctac | 1560 |
| aacaagaagt acacgtaccc gtggtgggc gatgccctgg gctggctcct ggctctgtcc | 1620 |
| tccatggtct gcattcctgc ctggagcctc tacagactcg gaaccctcaa gggcccttc | 1680 |
| agagagagaa tccgtcagct catgtgccca gccgaggacc tgccccagcg gaacccagca | 1740 |
| ggaccctcgg ctcccgccac ccccaggacc tcactgctca gactcacaga gctagagtct | 1800 |
| cactgc | 1806 |

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ggtgggatgg ataacagggt ctcgggaacg                                    30

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
ccctagcagt tagactccag ttctgtgagc                                    30

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gcacctcccc cattttttgta gcag                                         24

<210> SEQ ID NO 6
<211> LENGTH: 24
<212> TYPE: DNA
<213> ORGANISM: Artificial Sequence

```
-continued

<220> FEATURE:
<223> OTHER INFORMATION: Primer

<400> SEQUENCE: 6
gacaggaatg ccacaggtaa agag                                          24

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
ctctacagac tcggaaccct caag                                          24

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
cctgggctgg ctcctggctc tgtc                                          24

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ccatcctaat acgactcact atagggc                                       27

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
actcactata gggctcgagc ggc                                           23

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
ggcagcgcta gcaggtctgg cagcagcttc actaag                             36

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
tcaccagtcg acggcacaca ggcaccatcc aagggc                             36
```